United States Patent [19]

Imai et al.

[11] Patent Number: 4,916,080

[45] Date of Patent: Apr. 10, 1990

[54] IMMUNOASSAY WITH ANTIGEN OR ANTIBODY LABELLED MICROCAPSULES CONTAINING FLUORESCENT SUBSTANCE

[75] Inventors: Kyoko Imai, Katsuta; Yasushi Nomura, Mito, both of Japan

[73] Assignee: Hitachi, Ltd., Tokyo, Japan

[21] Appl. No.: 927,932

[22] Filed: Nov. 7, 1986

[30] Foreign Application Priority Data

Nov. 8, 1985 [JP] Japan .................. 60-248841

[51] Int. Cl.$^4$ ................ G01N 33/543; G01N 33/544; G01N 33/546; G01N 33/542

[52] U.S. Cl. ..................... 436/518; 436/528; 436/534; 436/537; 436/546; 436/800; 436/808; 436/821; 436/829

[58] Field of Search ............... 436/535, 536, 821, 829, 436/528, 518, 534, 537, 546, 800, 808

[56] References Cited

U.S. PATENT DOCUMENTS

| | | | |
|---|---|---|---|
| 4,429,230 | 1/1984 | Honkawa et al. | 250/461.2 |
| 4,483,921 | 11/1984 | Cole | 435/810 |
| 4,483,929 | 11/1984 | Szoka | 436/533 |
| 4,650,770 | 3/1987 | Liu et al. | 436/523 |

OTHER PUBLICATIONS

Patent Abstracts of Japan, vol. 9, No. 133 (P—362) (1856), Jun. 8, 1985; JP—A—60 17 359.
Biological Abstracts, vol. 76, No. 4, 1983, p. 2662, abstract no. 24645.

*Primary Examiner*—Robert J. Warden
*Assistant Examiner*—Jack Spiegel
*Attorney, Agent, or Firm*—Fay, Sharpe, Beall, Fagan, Minnich & McKee

[57] ABSTRACT

Microcapsules labeled with an antigen or antibody contain a liquid containing a fluorescent substance, for example, carboxyfluorescein. The liquid in the microcapsules is prepared so as to have a viscosity different from that of a liquid outside the microcapsules. For example, the microcapsules contain polyvinyl alcohol as a substance for increasing the viscosity. Antigen-antibody reaction is caused by mixing such microcapsules, a sample and a complement, and complement is activated with resulting antigen-antibody complex, whereby the microcapsules are lysed.

The reaction mixture is irradiated with exciting light, and the polarization components ($I_{\parallel}$ and $I_{\perp}$) of fluorescence from the reaction mixture are detected. The concentration of a substance to be assayed in the sample is determined by calculating the degree of polarization fluorescence P on the basis of the intensities of the polarization components.

According to this invention, the degree of polarization fluorescence of liquid before the immunoreaction is high but the degree of polarization fluorescence after the initiation of the immunoreaction is low. Therefore, immunoassay can be carried out with high accuracy.

42 Claims, 6 Drawing Sheets

IMMUNOASSAY WITH ANTIGEN OR ANTIBODY LABELLED MICROCAPSULES CONTAINING FLUORESCENT SUBSTANCE

BACKGROUND OF THE INVENTION

This invention relates to a method for immunoassay and reagents therefor, particularly to an analytical method and reagents therefor, which are suitable for assaying an antigen or an antibody in a body fluid sample by a polarization fluorescence method.

The previously known methods for measuring the concentration of an antigen or an antibody in a body fluid sample by fluorometry concern a method using microcapsules and a method utilizing polarization fluorescence. The method using microcapsules is shown, for example, in Japanese Patent Application Kokai (Laid-Open) No. 117159/85. In this method, carboxyfluorescein is encapsulated as a fluorescent compound in liposomes labeled with an antigen an antibody. This fluorescent compound undergoes self-quenching when its concentration is high, therefore by utilizing this property, it can be kept quenched while encapsulated in the liposomes. When the liposomes are lysed due to complement activated by the immune complexes resulting from the antigen-antibody reactions, the fluorescent compound flows out into the liquid outside the liposomes thereby decreasing in concentration and emitting fluorescence. The concentration of an antigen or an antibody in a sample is determined by measuring the intensity of the fluorescence produced.

Such a conventional method using microcapsules is not widely applicable because only fluorescent substances having self-quenching properties can be used.

On the other hand, an example of the method utilizing polarization fluorescence is shown, for example, in U.S. Pat. No. 4,429,230.

When fluorescent molecules are excited by polarized light, the orientation of the excited molecules is abolished by rotation of the molecules by Brownian motion during the period between light absorption and emission, so that the degree of polarization of fluorescence is lowered. When fluorescence intensities obtained when an polarizing plate on the exciting light side is vertically fixed and a polarizing plate on the fluorescence side is placed parallel or perpendicular thereto are taken as $I_\parallel$ and $I_\perp$ respectively, the degree of polarization fluorescence P is expressed by the formula:

$$P = \frac{I_\parallel - I_\perp}{I_\parallel + I_\perp} \quad (1)$$

When an antigen labeled with a fluorescent substance binds to the corresponding antibody, the molecules greatly increase in size, resulting in depression of rotary Brownian motion of the fluorescent molecules, and hence the degree of polarization becomes larger than that before the binding to the antibody. An assay utilizing the above-mentioned principle is polarization fluoroimmunoassay, which is as follows. When a fluorescence-labeled antigen is first reacted with an antibody and an unlabeled antigen (an unknown substance) to be determined is added to this system, the antibody is consumed so that the amount of labeled antigen binding to the antibody is reduced, and the amount of labeled antigen which does not bind to the antibody is increased. Since this labeled antigen has a low molecular weight, its rotary Brownian motion occurs actively, so that the degree of polarization is reduced. Therefore, the amount of the unknown substance can be determined from the extent of reduction of the degree of polarization.

In the case of the conventional immunoassay utilizing polarization fluorescence which is shown above, and in U.S. Pat. No. 4,429,230, the intensity of emission of fluorescence is low. Hence, it has been impossible to attain a high S/N ratio, wherein S indicates Signal and N indicates Noise.

SUMMARY OF THE INVENTION

The object of this invention is to remove the defects of the above-mentioned conventional methods, to provide an immunoassay method which is widely applicable and highly precise in measurement. A further object of the present invention is to provide for a reagent which can be used for said immunoassay method.

The immunoassay method of this invention comprises mixing microcapsules, a sample containing an antibody an antigen, and a complement, said microcapsules containing a fluid with a specific viscosity containing a fluorescent substance and being labeled with an antigen an antibody, causing an immunoreaction under the condition where the viscosity of the fluid in the microcapsules is different from that of a solution outside the microcapsules so that microcapsules are lysed by activated complement, irradiating the reaction mixture with exciting light, measuring polarization fluorescence due to the reaction mixture, and thereby determining the concentration of a target substance in the aforesaid sample.

In the reagent the immunoassay of this invention, microcapsules, labeled with an antigen or an antibody, are encapsulated with a fluid having a specific viscosity and containing a fluorescent substance, wherein said reagent is prepared so that the viscosity of a solution outside the microcapsules is different from that of the fluid inside the microcapsules. Complement may be either previously incorporated into the reagent or added to a sample solution at the time the sample is mixed with the reagent.

DETAILED DESCRIPTION OF THE PREFERRED EMBODIMENT

Figure 1:
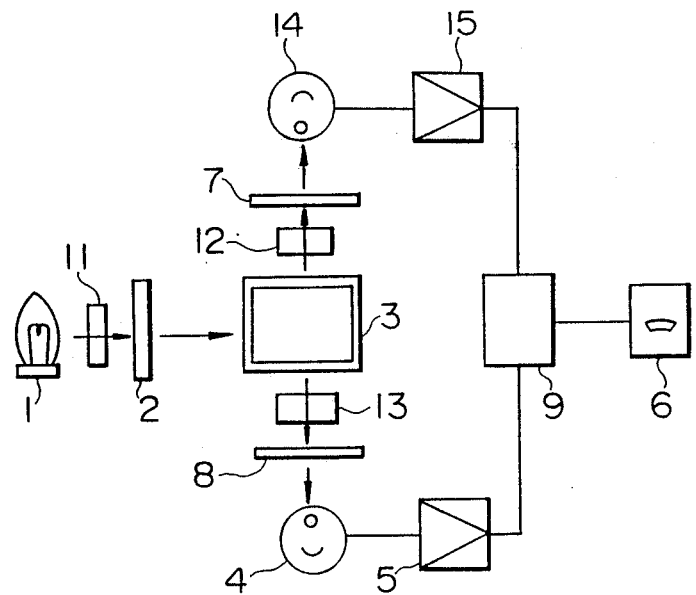
FIG. 1 shows one example of an analyzer suitable for conducting this invention.

The reagent for immunoassay according to this invention comprises a solution which contains microcapsules having a membrane labeled with an antigen or an antibody and containing a fluorescent substance therein. Moreover, the microcapsule undergoes lysis as a result of activated complement. As such a microcapsule, there can be used an erythrocyte of an animal, for example, sheep, and a The liposome which is an artificial membrane. Liposome can be prepared according to the method of T. T. Samuel et al. described in Methods in Enzymology, Vol. 74, pp. 152–161. These microcapsules can be labelled by attaching an antigen or an antibody on to the membranes. In addition, the microcapsules can contain a fluorescent substance. As the antibody or the antigen attached to the membrane, an antibody or an antigen which reacts specifically with an antigen or an antibody to be assayed in a sample, can be used. For example, when the substance in a sample to be assayed is insulin, anti-insulin antibody is attached to the membrane of microcapsule.

In the immunoassay according to this invention, there can be used for the assay, either microcapsules containing, as the fluorescent substance, a compound which does not undergo self-quenching even at a high concentration, such as fluorescein isothiocyanate (FITC), or microcapsules containing, as a fluorescent substance a compound which undergoes self-quenching, such as carboxyfluorescein.

The microcapsules are dispersed in a liquid, i.e., a buffer solution such as Tris-HCl buffer and veronal buffer.

According to this invention, the fluidity or viscosity of the fluid in the microcapsules is different from that of the liquid outside the microcapsules. In this regard, a viscosity modifier is used for increasing the viscosity inside or outside the microcapsules. The viscosity modifier is preferably a water-soluble organic compound having a viscosity higher than that of water, for example, polyvinyl alcohol, glycerin, sucrose, etc. The reagent is prepared so that one of the viscosities inside and outside of the microcapsules is higher than the other, and therefore when the microcapsule is lysed, as a result of complement activated with the immune complexes resulting from the antigen-antibody reactions, the fluorescent substance flows out of the microcapsules, and the fluidity around the fluorescent substance is changed. That is to say, since the degree of rotation freedom of the fluorescent substance is changed depending on whether the fluorescent substance is on the inside or the outside of the microcapsules, the polarization fluorescence characteristics are also changed.

For example, when the viscosity inside the microcapsules is made higher than that of the liquid (i.e., a buffer solution) outside the microcapsules, a buffer solution containing both a viscosity modifier and a fluorescent substance is encapsulated in the microcapsules. The viscosities of these liquids are largely dependent on temperature, but, for example, in an automated clinical analyzer, which is preferably used to conduct immunoassay of the present invention, they can be practically controlled because the temperature is maintained constant. The viscosity can be changed by properly selecting the kind and concentration of the viscosity modifier. Although the difference between viscosities inside and outside a usable microcapsule is dependent on the detection sensitivity for degree of polarization fluorescence of an analyzer, the viscosities are preferably adjusted so that the difference between them becomes 0.01 or more in terms of degree of polarization fluorescence.

There are disclosed below preferred embodiments according to this invention. The microcapsules contain a viscosity modifier. In an analyzer suitable for conducting immunoassay of this invention, a row of reaction cuvettes are placed on a turntable and each cuvette can freely be placed in a position for the addition of the reagent containing the microcapsules, a position for the addition of a sample, a position for the addition of a complement, and a position for photometry using a polarization fluorescence photometer.

First, the microcapsules and a sample are practically placed in a reaction cuvette, but no complement is placed therein. Therefore, the microcapsules are not lysed in the resulting mixture. The mixture is placed in the position for photometry and subjected to blank measurement. In detail, the mixture is irradiated with exciting light, after which the vertical-polarization component $I_{\parallel B}$ and the parallel-polarization component $I_{\perp B}$ of fluorescence from the mixture are detected and the degree of polarization fluorescence $P_B$ is calculated according to the above-mentioned equation (1). In the blank measurement, since the viscosity inside the microcapsules is high, Brownian motion of molecules of the fluorescent substance present therein is depressed, so that a high $P_B$ value is obtained. After the blank measurement, a complement is added to the mixture to initiate microcapsule lysis, and after a predetermined period of time, the reaction cuvette is once again placed in the position for photometry. When an antigen or an antibody attached as a label on the microcapsules reacts with an antibody or an antigen in the sample, the microcapsules are lysed by the activated complement activity, and the fluorescence substance in the microcapsules diffuses into a lower-viscosity liquid outside the microcapsules. With this lowering in viscosity, Brownian motion of the molecules of the fluorescent substance becomes active and the polarization fluorescence characteristics are diminished. The number of microcapsules lysed depends on the antibody or the antigen content of the sample. Therefore, the larger the antibody content of the sample, the smaller the degree of polarization fluorescence. Hence, quantitative analysis for a substance (e.g., antibody) to be assayed can be made possible by utilizing this technique.

The reaction cuvette containing the reaction solution in which microcapsule lysis is initiated is irradiated with exciting light, after which $I_{\parallel S}$ and $I_{\perp S}$ are detected and the degree of polarization fluorescence $P_S$ is calculated according to the equation (1). The higher the concentration of the substance to be assayed, the smaller the value of $P_S$. Subsequently, the measured values for the reaction solution (i.e., $I_{\parallel S}$ and $I_{\perp S}$) and the measured values for blank (i.e., $I_{\parallel B}$ and $I_{\perp B}$) are determined and the, P value is calculated according to below-mentioned equation (2) and compared with a previously prepared calibration curve, whereby the concentration of a substance to be assayed in the sample is determined.

When this invention is applied to the case where a liquid outside the microcapsules contains a viscosity modifier for increasing the viscosity, the behavior of the fluorescent substance is opposite to that in the above case. That is to say, while the fluorescent substance is kept inside the microcapsules, Brownian motion of its molecules is active, so that the degree of polarization fluorescence P is low, and when the fluorescent substance flows out of the microcapsules owing to activated complement resulting from immunoreaction, the Brownian motion is depressed by a high viscosity, so that the degree of polarization fluorescence P is increased. Therefore, the concentration of an antigen or antibody in a sample can be determined by measuring the degree of polarization fluorescence.

In one preferred embodiment of the invention, an antigen or an antibody in a test sample is allowed to react with an antibody or an antigen in competition with a known amount of antigen or antibody attached to the membranes of microcapsules, and thus the substance in the test sample is determined. That is to say, for example, a first reagent for immunoassay is prepared which is composed of a liquid containing antigen-labeled microcapsules and a complement. The microcapsules contain a fluorescent substance and viscosity modifier which forms a fluid having a viscosity higher than that of a solution outside the microcapsules, and a second reagent is prepared which contains an antibody which reacts specifically with the antigen to be determined.

First, the test-sample containing the antigen to be determined is mixed with the first reagent in a reaction vessel, and the second reagent is added to the reaction vessel. The antigen in the sample reacts with the antibody in the second reagent in competition with the antigen attached to the microcapsules. As a result of the antigen-antibody competitive reaction produced the microcapsules are lysed, and the fluorescent substance flows out of the microcapsules. The antigen in the sample is quantitated according to the polarization fluorescence method. The above-mentioned method is suitable for quantitating a substance having a relatively low molecular weight.

An outline of the structure of an analyzer suitable for conducting this invention is shown in FIG. 1. A sample cuvette 3 is used as a movable reaction vessel. The sample cuvette can be placed in the light-path of a photometer. Before the sample cuvette 3 is placed in the light-path, an antigen-antibody reaction is produced by placing in the sample cuvette a predetermined amount of a reagent solution which contains microcapsules containing a fluorecein series fluorescent substance and labeled with an antigen, followed by adding thereto a predetermined amount of blood sample containing the corresponding antibody and complement. Subsequently, the sample cuvette is placed in the light-path, of the photometer as shown in FIG. 1.

The sample cuvette 3 is irradiated with polarized light having the same specific wavelength as exciting light. The light from a light source 1 passes through an excitation wavelength selector 11 and then through a polarizing filter 2, and is cast on the cuvette 3. The walls of the cuvette in, at least, the direction of incidence of the exciting light and the two directions of taking out fluorescence, are made of a transparent material. The vertical-polarization component of fluorescence emitted by the sample is selectively transmitted by a vertical-polarization filter 7 which is fixed, and is received by a photodetector 14. The parallel-polarization component of fluorescence from the sample is selectively transmitted by a parallel-polarization filter 8 which is fixed, and is received by a photodetector 4. Fluorescence wavelength selectors 12 and 13 are placed in the fluorescence paths in the two directions, respectively, and the same fluorescence wavelengths are selected by them. Although the two fluorescence wavelength selectors are provided in FIG. 1, it is also possible to employ only one direction of taking out fluorescence, to select light having a specific wavelength, to divide its light-path in two, and to each of polarizing filters for taking out different polarization components in the two branch light-paths.

In either case, the photodetectors 4 and 14 can observe fluorescence from the same emission source at the same time. Each received light signal is amplified by an amplifier 5 or an amplifier 15 and subjected to calculation of the degree of polarization fluorescence in a computer 9. The calculation result is displayed in a display device 6 in terms of the concentration of a constituent to be assayed or the degree of polarization fluorescence.

As described more above in detail, in the method for immunoassay of this invention, the microcapsules labeled with an antigen or an antibody contain a liquid containing a fluorescent substance, and the liquid in the microcapsules is prepared so as to have a viscosity different from that of a liquid outside the microcapsules. Therefore, the immunoassay of this invention can be carried out with a high degree of accuracy.

According to this invention, either low-molecular weight substances or high-molecular-weight substances can be quantitated by a polarization fluorescence method. Moreover, a short-time, high-sensitivity assay can be easily realized because a large amount of a fluorescent substance can be encapsulated into the microcapsules as compared with the conventional methods.

In all of the conventional immunoassay processes using a polarization fluorescence method it has been difficult to quantitate a high-molecular-weight substance by a polarization fluorescence method.

Several examples according to this invention are described below.

EXAMPLE 1

There is described below one example of a method for preparing microcapsules composed of cell membranes of the erythrocytes of sheep, an antibody (e.g., sheep erythrocyte antibody) attached thereto, and a fluorescent substance (e.g., carboxyfluorescein) and viscosity modifier (e.g., polyvinyl alcohol) encapsulated in the erythrocytes. First, an isonic liquid (a buffer solution containing 0.15M sodium chloride, pH 7.4) containing sheep erythrocytes suspended therein was mixed with sheep erythrocyte antibody (commercially available) to adsorb the sheep erythrocyte antibody onto the cell membranes of the sheep erythrocytes. Next, cell sap and the like were discharged from the erythrocytes by a conventional method, i.e., dialysis, and a liquid containing carboxyfluorescein and polyvinyl alcohol (PVA) was encapsulated into the erythrocytes. The concentrations of carboxyfluorescein and PVA in this case were properly determined depending on the immunoassay method.

As the complement in the reagent, those contained in animal bloods could be used. For example, serum of guinea pig could be used as it is as a complement-containing liquid.

EXAMPLE 2

In this example, an antigen in a test sample, for example, an antigen in blood was determined. As the microcapsules in a reagent, there were used those composed of a membrane and an antibody attached thereon which reacted specifically with the antigen in the sample.

These microcapsules contained a fluorescent substance and glycerin for increasing the viscosity. The reagent solution contained a complement in addition to the microcapsules. The liquid outside the microcapsules contained no glycerine and hence had a low viscosity.

Liposomes, as microcapsules, having an antigen attached thereto were prepared by a method according to the method of T. T. Samuel et al. described in Methods in Enzymology, Vol. 74, pp. 152-161. As the complement, the same complement as utilized in Example 1 was used.

First, the test sample and the reagent were placed in a reaction vessel and mixed. The complement was activated by the antigen-antibody reaction produced, whereby the microcapsules were lysed and the fluorescent substance flowed out thereof. The amount of the fluorescent substance flowed out thereof. The amount of the fluorescent substance having flowed out of the microcapsules varied depending on the amount of antigen in the sample. Further, the rotation of fluorescent molecules was depressed in the microcapsules because the viscosity therein was maintained at an increased level, but when the microcapsules were lysed by the activated complement and the fluorescent substance flowed out thereof, the fluorescent molecules were abled to rotate freely.

After a predetermined period of time, the reaction mixture was irradiated with exciting light. The differences between blank $P_B$ and reaction mixture $P_S$ [i.e., $(I_{\parallel S} - I_{\parallel B})$ and $(I_{\perp S} - I_{\perp B})$] were measured, P value was calculated according to the following equation (2)

$$P = \frac{(I_{\parallel S} - I_{\parallel B}) - (I_{\perp S} - I_{\perp B})}{(I_{\parallel S} - I_{\parallel B}) + (I_{\perp S} - I_{\perp B})} \quad (2)$$

and the antigen concentration in the sample was calculated. A calibration curve was prepared by previously subjecting standard samples containing known concentrations of the antigen to measurement, and inputting the measurement results in a control and storage unit of an analyzer. The calibration curve produced was used for calculating the test sample.

Figure 2:
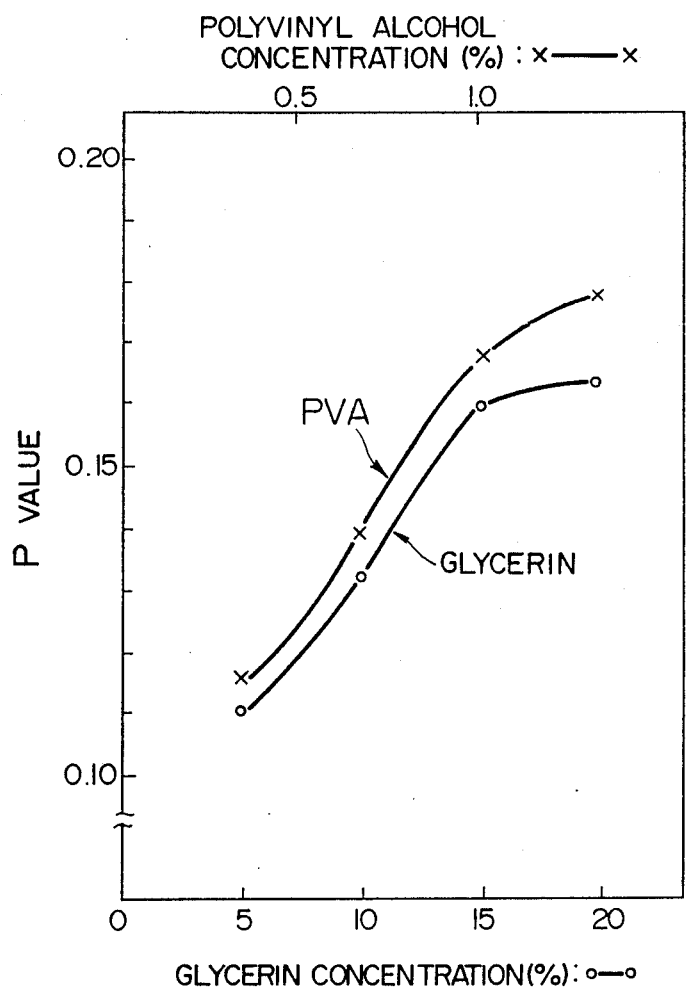
FIG. 2 is a graph showing the relationship between the concentration of the viscosity modifier and the degree of polarization fluorescence.

The results produced demonstrating the relationship between the concentration of the viscosity modifier and the degree of polarization fluorescence in the case of a liquid containing a viscosity modifier and a fluorescent substance which was to be encapsulated in liposome were determined. Glycerin or polyvinyl alcohol (PVA) was used as the viscosity modifier, and an aqueous carboxyfluorescein solution as the fluorescent substance. The results obtained are shown in FIG. 2.

EXAMPLE 3

The third example, according to this invention is suitable for quantitating a substance having a relatively low molecular weight by a polarization fluorescence method. In this example, antigen in a test sample and antigen attached to the membranes of microcapsules are competitively reacted with antibody. A first reagent for immunoassay was composed of a liquid containing antigen (Thyroxine=$T_4$) labeled microcapsules and a complement (serum of guinea pig). The microcapsules contained a fluorescent substance (carboxyfluorescein) and polyvinyl alcohol which formed a fluid having a viscosity higher than that of a solution outside the microcapsules. A second reagent contained an antibody (anti-$T_4$ antibody) which reacts specifically with the antigen ($T_4$) to be determined.

First, the test-sample containing the antigen ($T_4$) to be determined were mixed with the first reagent in a reaction vessel, and the second reagent was added to the reaction vessel, and the second reagent was added to the reaction vessel. The antigen ($T_4$) in the sample reacted with the antibody (anti-$T_4$ antibody) in the second reagent in competition with the antigen ($T_4$) attached to the microcapsules. As a result of the complement activated by the antigen-antibody reaction, which caused the microcapsules to be lysed, the fluorescent substance flowed out of the microcapsules. The antigen in the sample was quantitated by calculating T value according to equation (2) in the same way as Example 2.

Thyroxine ($T_4$) having a molecular weight of 777 was used as the low-molecular-weight substance.

EXAMPLE 4

There is described below one example of immunoassay according to the same method as Example 3.

Figure 3:
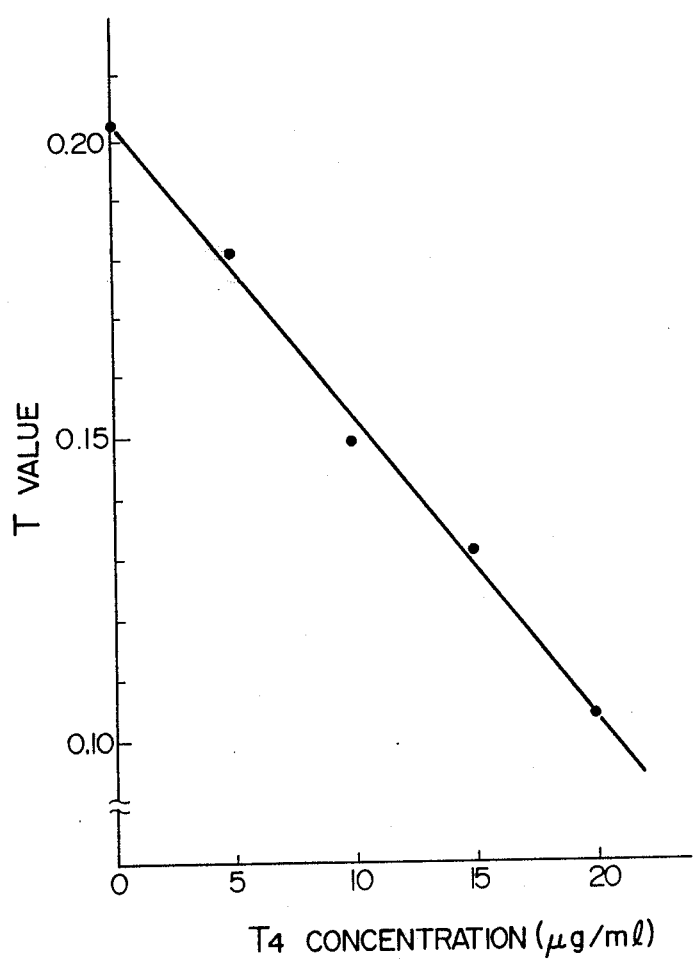
FIG. 3 is a graph showing one example of calibration curve for quantitating Thyroxine (T4).

Sheep erythrocytes, prepared in the same manner as in the Example 1 were used as the microcapsules, and carboxyfluorescein was used as the fluorescent substance. A buffer solution containing 0.8% polyvinyl alcohol was used as a fluid to be contained in microcapsules. In this regard 10 μl of the sample containing $T_4$ to be measured was mixed with 25 μl of anti-$T_4$ antibody, 50 μl of a sheep erythrocyte reagent having $T_4$ attached thereto, 15 μl of complement (serum of guinia pig, and 900 μl of 0.05M Tris-HCl buffer (pH 7.4). The resulting mixture was subjected to reaction at 37° C. for 15 minutes. Subsequently, the degree of abolishment of polarization fluorescence in the reaction solution was measured. In this case, the wavelength of exciting light was 495 nm, and the wavelength of fluorescence was 515 nm. $I_\parallel$ and $I_\perp$ were measured, after which the degree of polarization fluorescence was calculated according to the equation (1), and the $T_4$ concentration was determined by comparing the degree of diminished of polarization fluorescence with a previously prepared calibration curve. The calibration curve used is shown in FIG. 3.

EXAMPLE 5

There is described below one example of immunoassay according to the same method as Example 2.

Figure 4:
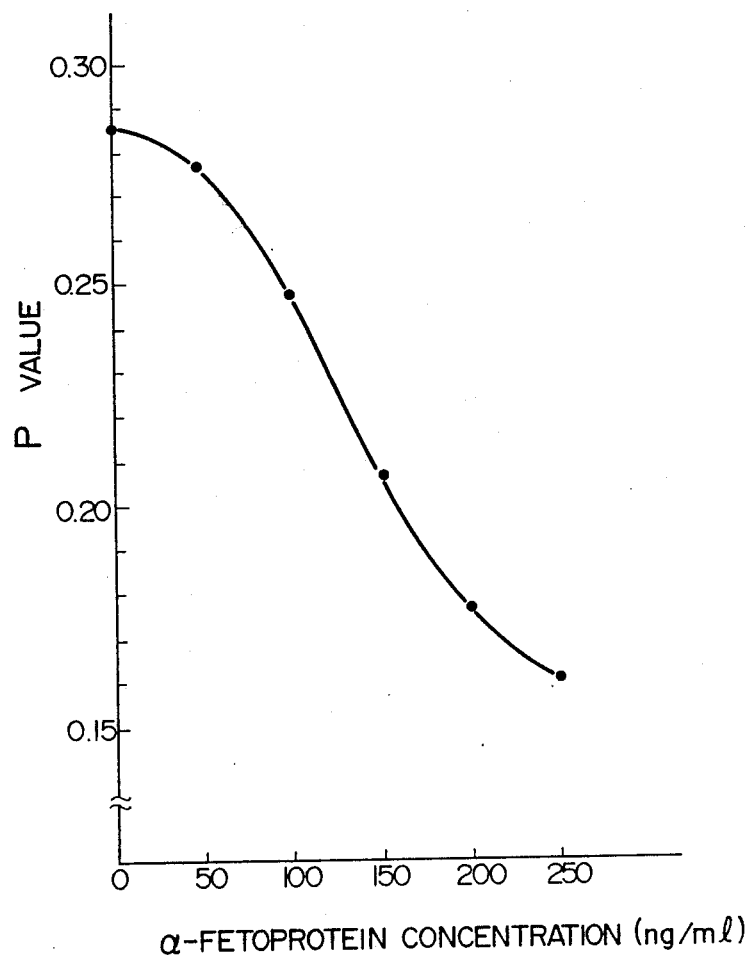
FIG. 4 is a graph showing one example of calibration curve for quantitating α-fetoprotein in the case where carboxyfluorescein is encapsulated in the liposomes.

In this example, α-fetoprotein having a molecular weight of about 70,000 was determined as the high-molecular-weight substance. A buffer solution (pH 7.4) containing PVA and carboxyfluorescein was encapsulated in the microcapsules. Liposomes made of sphingomyelin, which were prepared according to Example 2, were used as the microcapsules, and 0.8% polyvinyl alcohol was used as the viscosity modifier. In this regard, the 10 μl of sample containing the α-fetoprotein to be measured was mixed with 50 μl of a liposome having anti-α-fetoprotein antibody attached thereto, 15 μl of a complement (serum of guinea pig) and 925 μl of 0.05M tris-HCl buffer (pH 7.4). The resulting mixture was subjected to reaction at 37° C. for 15 minutes. Subsequently, the degree of diminished polarization fluorescence in the reaction solution was measured. The calibration curve used for this measurement is shown in FIG. 4.

EXAMPLE 6

Figure 6:
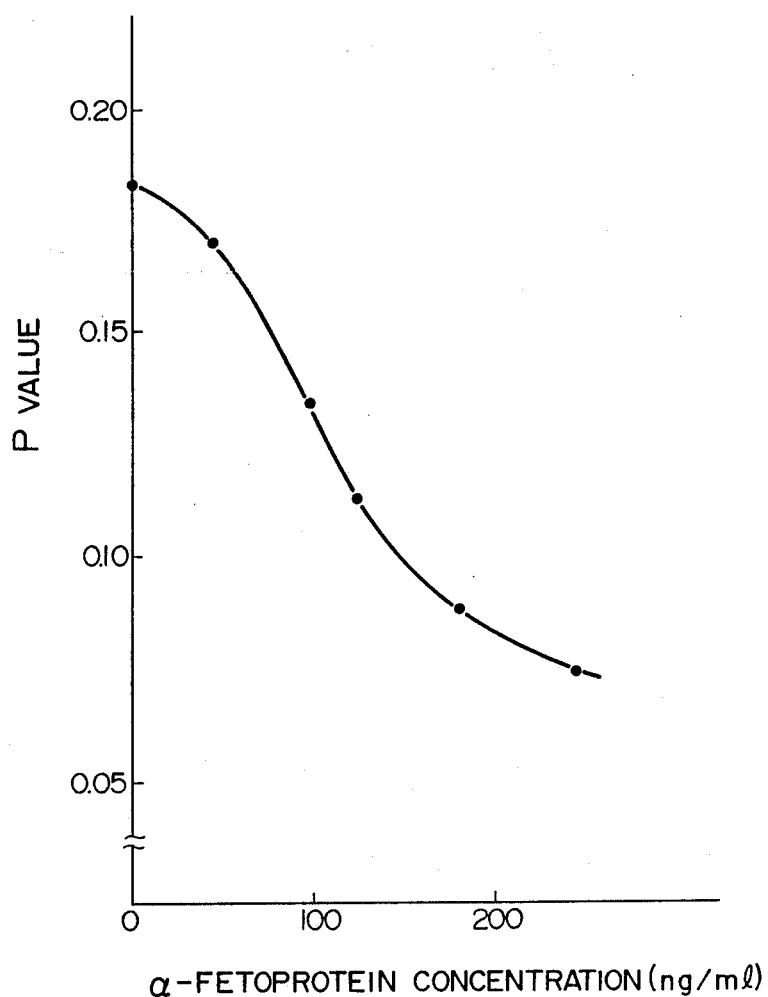
FIG. 6 is a graph showing one example of a calibration curve for quantitating α-fetoprotein in the case where fluorescein isothiocyanate is encapsulated in the liposomes.

A high viscosity solution was prepared by dissolving fluorescein isothiocyanate (FITC) as a fluorescent substance in a veronal buffer (pH 7.4) containing 15% of glycerin as a viscosity modifier. Liposomes made of sphingomyelin were prepared according to the Procedure set forth in Example 2 so as to contain the high-viscosity solution. An anti-α-feto-protein antibody was attached to the membranes of the liposomes. In a reaction vessel, 10 μl of the liposome reagent, 20 μl of a sample containing α-feto-protein, 10 μl of complement (serum of guinea pig) and 970 μl of 5 mM veronal buffer (pH 7.4), were mixed, and the immunoreactin was initiated. The reaction solution was incubated at 37° C. for 15 minutes and then the degree of diminished polarization fluorescence was determined. The calibration curve used for this determination is shown in FIG. 6.

EXPERIMENTAL EXAMPLE

A liposome reagent was prepared in the same manner as in Example 5. Samples prepared by adding various concentrations of α-fetoprotein to serum of a patient were subjected to the same analytical procedure as set forth in the Example 5. The recovery (%) after addition was determined by comparing the determination result of α-fetoprotein with the amount added. The results obtained are shown in Table 1. Results obtained according to a conventional liposome method are also shown in Table 1.

TABLE 1

| | | Recovery (%) after addition of α-fetoprotein | | | |
|---|---|---|---|---|---|
| | | The present method | | Conventional process | |
| Patient's sample | Adding concentration | Measured value | Recovery | Measured value | Recovery |
| A | 50.0 mg/ml | 50.5 mg/ml | 101% | 45.8 mg/ml | 92% |
| B | 100.0 | 101.0 | 101 | 42.0 | 42 |
| C | 100.0 | 99.5 | 100 | 68.0 | 68 |
| D | 100.0 | 102.0 | 102 | 72.0 | 72 |

Figure 5:
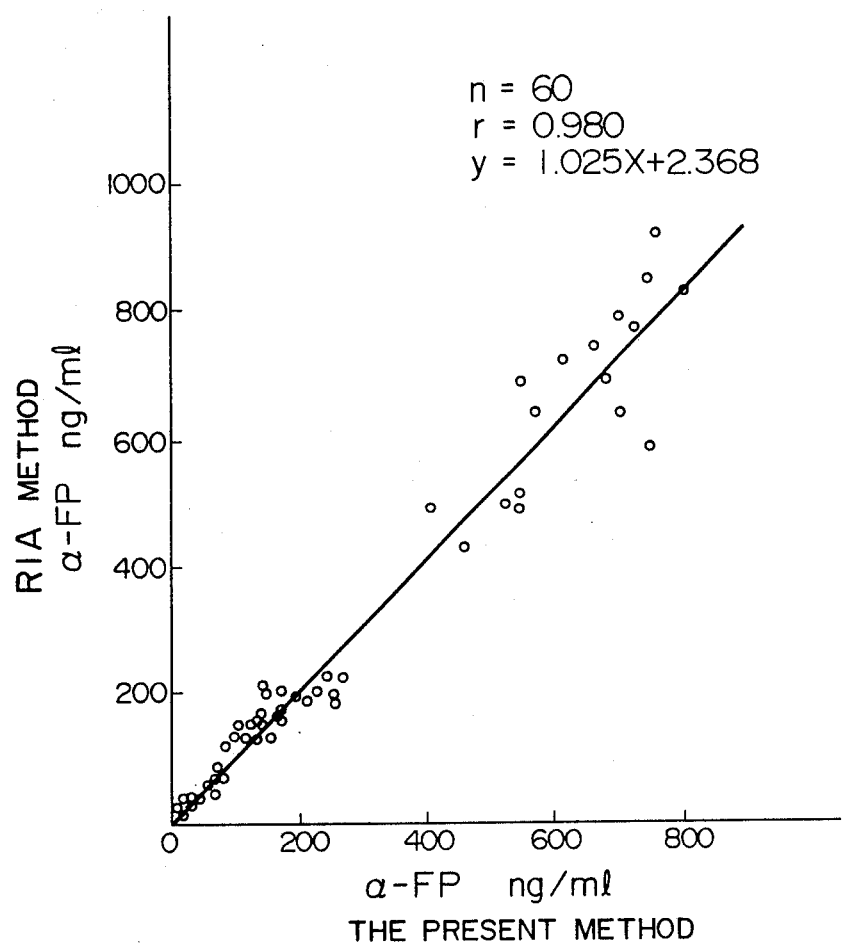
FIG. 5 is a graph showing the correlation for α-fetoprotein between a measured value obtained according to this invention and those obtained according to a conventional RIA process.

Next, the correlation between the method according to this invention and a conventional radioimmunoassay (RIA) is shown in FIG. 5. Sixty patients' sera were subjected to measurement by each of these processes. In the case of the present method, the α-fetoprotein concentration was measured according to Example 5. Samples having a high concentration were used after proper dilution with physiological saline. The present process had satisfactory correlation with the RIA process.

What is claimed is:

1. An immunoassay method for determining the concentration of an antigen in a test sample, comprising the steps of:
   (a) mixing microcapsules labelled with an antibody for the antigen being tested for with a sample to produce a mixture; wherein said microcapsules (i) contain a fluid having a viscosity different from that of the mixture outside the microcapsules; (ii) contain a fluorescent substance; and, (iii) are susceptible to lysis upon complement activated immunoreaction;
   (b) irradiating said mixture with excited light and detecting the vertical-polarization component $I_{\parallel B}$ and the parallel-polarization component $I_{\perp B}$ of fluorescence from the mixture;
   (c) adding complement to the mixture to initiate lysis of the microcapsules wherein the number of microcapsules lysed is dependent upon the antigen concentration of the sample;
   (d) irradiating the reaction mixture with excited light and detecting the vertical-polarization component $I_{\parallel B}$ and the parallel-polarization component $I_{\perp B}$ of fluorescence from the reaction mixture;
   (e) comparing the detection results of the vertical-polarization component of $I_{\parallel B}$ and the parallel-polarization component $I_{\perp B}$ of fluorescence from the mixture with the vertical-polarization component $I_{\parallel B}$ and the parallel-polarization component $I_{\perp B}$ of fluorescence from the reaction mixture to determine the change in the degree of polarization fluorescence due to the lysis of the microcapsules; and,
   (f) comparing the change in the degree of polarization fluorescence with a calibration curve which was previously prepared by subjecting standard samples containing known concentrations of the antigen to change in polarization fluorescence measurements, thereby determining the concentration of the antigen in the test sample.

2. The immunoassay method of claim 1, wherein said microcapsules contain a viscosity modifier in sufficient concentration to make the viscosity of the fluid inside said microcapsules higher than the viscosity of the mixture outside said microcapsules.

3. The immunoassay method of claim 1, wherein the mixture outside said microcapsules contains a viscosity modifier in a sufficient concentration to make the viscosity of the fluid inside said microcapsules lower than the viscosity of the mixture outside said microcapsules.

4. The immunoassay method of claim 2, wherein said viscosity modifier is a water-soluble organic compound having a viscosity higher than that of water.

5. The immunoassay method of claim 3, wherein said viscosity modifier is a water-soluble organic compound having a viscosity higher than that of water.

6. The immunoassay method of claim 4, wherein said viscosity modifier is selected from the group consisting of polyvinyl alcohol, glycerin and sucrose.

7. The immunoassay method of claim 5, wherein said viscosity modifier is selected from the group consisting of polyvinyl alcohol, glycerin and sucrose.

8. An immunoassay method for determining the concentration of an antibody in a test sample, comprising the steps of:
   (a) mixing microcapsules labelled with an antigen for the antibody being tested for with a sample to produce a mixture; wherein said microcapsules (i) contain a fluid having a viscosity different from that of the mixture outside the microcapsules; (ii) contain a fluorescent substance; and, (iii) are susceptible to lysis upon complement activated immunoreaction;
   (b) irradiating said mixture with excited light and detecting the vertical-polarization component $I_{\parallel B}$ and the parallel-polarization component $I_{\perp B}$ of fluorescence from the mixture;

(c) adding complement to the mixture to initiate lysis of the microcapsules wherein the number of microcapsules lysed is dependent upon the antibody concentration of the sample;

(d) irradiating the reaction mixture with excited light and detecting the vertical-polarization component $I_{\parallel B}$ and the parallel-polarization component $I_{\perp B}$ of fluorescence from the reaction mixture;

(e) comparing the detection results of the vertical-polarization component of $I_{\parallel B}$ and the parallel-polarization component $I_{\perp B}$ of fluorescence from the mixture with the vertical-polarization component $I_{\parallel B}$ and the parallel-polarization component $I_\perp$ of fluorescence from the reaction mixture to determine the change in the degree of polarization fluorescence due to the lysis of the microcapsules; and, (f) comparing the change in the degree of polarization fluorescence with a calibration curve which was previously prepared by subjecting standard samples containing known concentrations of the antibody to change in polarization fluorescence measurements, thereby determining the concentration of the antibody in the test sample.

9. The immunoassay method of claim 8, wherein said microcapsules contain a viscosity modifier in sufficient concentration to make the viscosity of the fluid inside said microcapsules higher than the viscosity of the mixture outside said microcapsules.

10. The immunoassay method of claim 8, wherein the mixture outside said microcapsules contains a viscosity modifier in a sufficient concentration to make the viscosity of the fluid inside said microcapsules lower than the viscosity of the mixture outside said microcapsules.

11. The immunoassay method of claim 9, wherein said viscosity modifier is a water-soluble organic compound having a viscosity higher than that of water.

12. The immunoassay method of claim 10, wherein said viscosity modifier is a water-soluble organic compound having a viscosity higher than that of water.

13. The immunoassay method of claim 11, wherein said viscosity modifier is selected from the group consisting of polyvinyl alcohol, glycerin, and sucrose.

14. The immunoassay method of claim 12, wherein said viscosity modifier is selected from the group consisting of polyvinyl alcohol, glycerin, and sucrose.

15. An immunoassay method for determining the concentration of an antigen in a test sample, comprising the steps of:
(a) mixing microcapsules labelled with an antibody for the antigen being tested for with complement to produce a mixture; wherein said microcapsules (i) contain a fluid having a viscosity different from that of the mixture outside the microcapsules; (ii) contain a fluorescent substance; and, (iii) are susceptible to lysising upon complement activated immunoreaction;
(b) irradiating said mixture with excited light and detecting the vertical-polarization component $I_{\parallel B}$ and the parallel-polarization component $I_{\perp B}$ of fluorescence from the mixture;
(c) adding a sample to be tested to the mixture to initiate lysis of the microcapsules by the activated complement-antibody-antigen reaction wherein the number of microcapsules lysed are dependent upon the antigen concentration of the sample;
(d) irradiating the reaction mixture with excited light and detecting the vertical-polarization component $I_{\parallel B}$ and the parallel-polarization component $I_{\perp B}$ of fluorescence from the reaction mixture; and,
(e) comparing the detection results of the vertical-polarization component of $I_{\parallel B}$ and the parallel-polarization component $I_{\perp B}$ of fluorescence from the mixture with the vertical-polarization component $I_{\parallel B}$ and the parallel-polarization component $I_{\perp B}$ of fluorescence from the reaction mixture to determine the change in the degree of polarization fluorescence due to the lysis of the microcapsules; and,
(f) comparing the change in the degree of polarization fluorescence with a calibration curve which was previously prepared by subjecting standard samples containing known concentrations of the antigen to change in polarization fluorescence measurements, thereby determining the concentration of the antigen in the test sample.

16. The immunoassay method of claim 15, wherein said microcapsules contain a viscosity modifier in sufficient concentration to make the viscosity of the fluid inside said microcapsules higher than the viscosity of the mixture outside said microcapsules.

17. The immunoassay method of claim 15, wherein the mixture outside said microcapsules contains a viscosity modifier in a sufficient concentration to make the viscosity of the fluid inside said microcapsules lower than the viscosity of the mixture outside said microcapsules.

18. The immunoassay method of claim 16, wherein said viscosity modifier is a water-soluble organic compound having a viscosity higher than that of water.

19. The immunoassay method of claim 17, wherein said viscosity modifier is a water-soluble organic compound having a viscosity higher than that of water.

20. The immunoassay method of claim 18, wherein said viscosity modifier is selected from the group consisting of polyvinyl alcohol, glycerin and sucrose.

21. The immunoassay method of claim 19, wherein said viscosity modifier is selected from the group consisting of polyvinyl alcohol, glycerin, and sucrose.

22. An immunoassay method for determining the concentration of an antibody in a test sample, comprising the steps of:
(a) mixing microcapsules labelled with an antigen for the antibody being tested for with complement to produce a mixture; wherein said microcapsules (i) contain a fluid having a viscosity different from that of the mixture outside the microcapsules; (ii) contain a fluorescent substance; and, are susceptible to lysis upon complement activated immunoreaction;
(b) irradiating said mixture with excited light and detecting the vertical-polarization component $I_{\parallel B}$ and the parallel-polarization component $I_{\perp B}$ of fluorescence from the mixture;
(c) adding a sample to be tested to the mixture to initiate lysis of the microcapsules by the activated complement-antibody-antigen reaction wherein the number of microcapsules lysed is dependent upon the antibody concentration of the sample;
(d) irradiating the reaction mixture with excited light and detecting the vertical-polarization component $I_{\parallel B}$ and the parallel-polarization component $I_{\perp B}$ of fluorescence from the reaction mixture;

(e) comparing the detection results of the vertical-polarization component of $I_{\|B}$ and the parallel-polarization component $I_{\perp B}$ of fluorescence from the mixture with the vertical-polarization component $I_{\|B}$ and the parallel-polarization component $I_{\perp B}$ of fluorescence from the reaction mixture to determine the change in the degree of polarization fluorescence due to the lysis of the microcapsules; and, (f) comparing the change in the degree of polarization fluorescence with a calibration curve which was previously prepared by subjecting standard samples containing known concentrations of the antibody to change in polarization fluorescence measurements, thereby determining the concentration of the antibody in the test sample.

23. The immunoassay method of claim 22, wherein said microcapsules contain a viscosity modifier in sufficient concentration to make the viscosity of the fluid inside said microcapsules higher than the viscosity of the mixture outside said microcapsules.

24. The immunoassay method of claim 22, wherein the mixture outside said microcapsules contains a viscosity modifier in a sufficient concentration to make the viscosity of the fluid inside said microcapsules lower than the viscosity of the mixture outside said microcapsules.

25. The immunoassay method of claim 23, wherein said viscosity modifier is a water-soluble organic compound having a viscosity higher than that of water.

26. The immunoassay method of claim 24, wherein said viscosity modifier is a water-soluble organic compound having a viscosity higher than that of water.

27. The immunoassay method of claim 25, wherein said viscosity modifier is selected from the group consisting of polyvinyl alcohol, glycerin and sucrose.

28. The immunoassay method of claim 26, wherein said viscosity modifier is selected from the group consisting of polyvinyl alcohol, glycerin and sucrose.

29. An immunoassay method for determining the concentration of an antigen in a test sample, comprising the steps of:

(a) mixing microcapsules labelled with an antibody for the antigen being tested for with a sample to produce a mixture; wherein said microcapsules (i) contain a fluid, a fluorescent substance, and, a viscosity modifier which modifies the viscosity of the fluid contained inside the microcapsules to a viscosity different from that of the mixture outside of the microcapsules; and, (ii) are susceptible to lysis upon complement activated immunoreaction;

(b) irradiating said mixture with excited light;

(c) detecting the vertical-polarization component $I_{\|B}$ and the parallel-polarization component $I_{\perp B}$ of fluorescence from the mixture;

(d) calculating the degree of polarization fluorescence $P_B$ of the mixture by the equation:

$$P_B = \frac{I_\| - I_\perp}{I_\| + I_\perp};$$

(e) adding complement to the mixture to initiate lysis of the microcapsules by the activated complement-antibody-antigen reaction wherein the number of microcapsules lysed is dependent upon the antigen concentration of the sample;

(f) irradiating the reaction mixture with excited light;

(g) detecting the vertical-polarization component $I_{\|B}$ and the parallel-polarization component $I_{\perp B}$ of fluorescence from the reaction mixture;

(h) calculating the degree of polarization fluorescence $P_B$ of the reaction mixture by the equation:

$$P_B = \frac{I_\| - I_\perp}{I_\| + I_\perp};$$

(i) comparing the degree of polarization fluorescence $P_B$ of the mixture with the degree of polarized fluorescence $P_B$ of the reaction mixture to determine the change in the degree of polarization fluorescence due to the lysis of the microcapsules; and, (j) comparing the change in the degree of polarization fluorescence with a calibration curve which was previously prepared by subjecting standard samples containing known concentration of the antigen to change in polarization fluorescence measurements, thereby determining the concentration of the antigen in the test sample.

30. The immunoassay method of claim 29, wherein said viscosity modifier is present in the microcapsules in a sufficient concentration to make the viscosity of the fluid inside said microcapsules higher than the viscosity of the mixture outside said microcapsules.

31. The immunoassay method of claim 30, wherein said modifier is present in the microcapsules in a sufficient concentration to make the viscosity of the fluid inside said microcapsules greater than 0.01, in terms of degree of polarization fluorescence, the viscosity of the mixture outside said microcapsules.

32. An immunoassay method for determining the concentration of an antibody in a test sample, comprising the steps of:

(a) mixing microcapsules labelled with an antigen for the antibody being tested for with a sample to produce a mixture; wherein said microcapsules (i) contain a fluid, a fluorescent substance, and, a viscosity modifier which modifies the viscosity of the fluid contained inside the microcapsules to a viscosity different from that of the mixture outside of the microcapsules; and, (ii) are susceptible to lysis upon complement activated immunoreaction;

(b) irradiating said mixture with excited light;

(c) detecting the vertical-polarization component $I_{\|B}$ and the parallel-polarization component $I_{\perp B}$ of fluorescence from the mixture;

(d) calculating the degree of polarization fluorescence $P_B$ of the mixture by the equation:

$$P_B = \frac{I_\| - I_\perp}{I_\| + I_\perp};$$

(e) adding complement to the mixture to initiate lysis of the microcapsules by the activated complement-antibody-antigen reaction wherein the number of microcapsules lysed is dependent upon the antibody concentration of the sample;

(f) irradiating the reaction mixture with excited light;

(g) detecting the vertical-polarization component $I_{\|B}$ and the parallel-polarization component $I_{\perp B}$ of fluorescence from the reaction mixture;

(h) calculating the degree of polarization fluorescence $P_B$ of the reaction mixture by the equation:

$$P_B = \frac{I_\| - I_\perp}{I_\| + I_\perp};$$

(i) comparing the degree of polarization fluorescence $P_B$ of the mixture with the degree of polarized fluorescence $P_B$ of the reaction mixture to determine the change in the degree of polarization fluorescence due to the lysis of the microcapsules; and, (j) comparing the change in the degree of polarization fluorescence with a calibration curve which was previously prepared by subjecting standard samples containing known concentrations of the antibody to change in polarization fluorescence measurements, thereby determining the concentration of the antibody in the test sample.

33. The immunoassay method of claim 32, wherein said viscosity modifier is present in the microcapsules in a sufficient concentration to make the viscosity of the fluid inside said microcapsules higher than the viscosity of the mixture outside said microcapsules.

34. The immunoassay method of claim 32, wherein said modifier is present in the microcapsules in a sufficient concentration to make the viscosity of the fluid inside said microcapsules greater than 0.01, in terms of degree of polarization fluorescence, the viscosity of the mixture outside said microcapsules.

35. An immunoassay method for determining the concentration of an antigen in a test sample, comprising the steps of:

(a) mixing microcapsules labelled with an antibody for the antigen being tested for with complement to produce a mixture; wherein said microcapsules (i) contain a fluid, a fluorescent substance, and, a viscosity modifier which modifies the viscosity of the fluid contained inside the microcapsules to a viscosity different from that of the mixture outside of the microcapsules; and, (ii) are susceptible to lysis upon complement activated immunoreaction;

(b) irradiating said mixture with excited light;

(c) detecting the vertical-polarization component $I_{\|B}$ and the parallel-polarization component $I_{\perp B}$ of fluorescence from the mixture;

(d) calculating the degree of polarization fluorescence $P_B$ of the mixture by the equation:

$$P_B = \frac{I_\| - I_\perp}{I_\| + I_\perp};$$

(e) adding a sample to be tested to the mixture to initiate lysis of the microcapsules by the activated complement-antibody-antigen reaction wherein the number of microcapsules lysed is dependent upon the antigen concentration of the sample;

(f) irradiating the reaction mixture with excited light;

(g) detecting the vertical-polarization component $I_{\|B}$ and the parallel-polarization component $I_{\perp B}$ of fluorescence from the reaction mixture;

(h) calculating the degree of polarization fluorescence $P_B$ of the reaction mixture by the equation:

$$P_B = \frac{I_\| - I_\perp}{I_\| + I_\perp};$$

(i) comparing the degree of polarization fluorescence $P_B$ of the mixture with the degree of polarized fluorescence of the reaction mixture to determine the change in the degree of polarization fluorescence due to the lysis of the microcapsules; and, (j) comparing the change in the degree of polarization fluorescence with a calibration curve which was previously prepared by subjecting standard samples containing known concentrations of the antigen to change in polarization fluorescence measurements, thereby determining the concentration of the antigen in the test sample.

36. The immunoassay method of claim 35, wherein said viscosity modifier is present in the microcapsules in a sufficient concentration to make the viscosity of the fluid inside said microcapsules higher than the viscosity of the mixture outside said microcapsules.

37. The immunoassay method of claim 35, wherein said modifier is present in the microcapsules in a sufficient concentration to make the viscosity of the fluid inside said microcapsules greater than 0.01, in terms of degree of polarization fluorescence, the viscosity of the mixture outside said microcapsules.

38. An immunoassay method for determining the concentration of an antibody in a test sample, comprising the steps of:

(a) mixing microcapsules labelled with an antigen for the antibody being tested for with complement to produce a mixture; wherein said microcapsules (i) contain a fluid, a fluorescent substance, and, a viscosity modifier which modifies the viscosity of the fluid contained inside the microcapsules to a viscosity different from that of the mixture outside of the microcapsules; and, (ii) are susceptible to lysis upon complement activated immunoreaction;

(b) irradiating said mixture with excited light;

(c) detecting the vertical-polarization component $I_{\|B}$ and the parallel-polarization component $I_{\perp B}$ of fluorescence from the mixture;

(d) calculating the degree of polarization fluorescence $P_B$ of the mixture by the equation:

$$P_B = \frac{I_\| - I_\perp}{I_\| + I_\perp};$$

(e) adding a sample to be tested to the mixture to initiate lysis of the microcapsules by the activated complement-antibody-antigen reaction wherein the number of microcapsules lysed is dependent upon the antibody concentration of the sample;

(f) irradiating the reaction mixture with excited light;

(g) detecting the vertical-polarization component $I_{\|B}$ and the parallel-polarization component $I_{\perp B}$ of fluorescence from the reaction mixture;

(h) calculating the degree of polarization fluorescence $P_B$ of the reaction mixture by the equation:

$$P_B = \frac{I_\| - I_\perp}{I_\| + I_\perp};$$

(i) comparing the degree of polarization fluorescence $P_B$ of the mixture with the degree of polarized fluorescence of the reaction mixture to determine the change in the degree of polarization fluorescence due to the lysis of the microcapsules; and, (j) comparing the change in the degree of polarization fluorescence with a calibration curve which was previously prepared by subjecting standard samples containing known concentrations of the antibody to change in polarization fluorescence measurements, thereby determining the concentration of the antibody in the test sample.

39. The immunoassay method of claim 38, wherein said viscosity modifier is present in the microcapsules in a sufficient concentration to make the viscosity of the fluid inside said microcapsules higher than the viscosity of the mixture outside said microcapsules.

40. The immunoassay method of claim 38, wherein said modifier is present in the microcapsules in a sufficient concentration to make the viscosity of the fluid inside said microcapsules greater than 0.01, in terms of degree of polarization fluorescence, the viscosity of the mixture outside said microcapsules.

41. An immunoassay test kit for determining the concentration of an antigen in a test sample, said test kit comprising:
a container carrying microcapsules labelled with an antibody for the antigen being tested for, and complement, wherein said microcapsules (i) contain a fluid having a viscosity different from that of the test sample; (ii) contain a fluorescent substance; and, (iii) are susceptible to lysis upon complement activated immunoreaction.

42. An immunoassay test kit for determining the concentration of an antibody in a test sample, said test kit comprising:
a container carrying microcapsules labelled with an antigen for the antibody being tested for, and complement, wherein said microcapsules, (i) contain a fluid having a viscosity different from that of the test sample; (ii) contain a fluorescent substance; and, (iii) are susceptible to lysis upon complement activated immunoreaction.

* * * * *